United States Patent [19]

Yoshida et al.

[11] Patent Number: 5,219,805
[45] Date of Patent: Jun. 15, 1993

[54] IVORY-COLORED ZIRCONIA SINTERED BODY, PROCESS FOR ITS PRODUCTION AND ITS USE

[75] Inventors: Masahiro Yoshida, Hidaka; Nobuo Kimura, Oiso; Hiromichi Okamura, Fujishiro, all of Japan

[73] Assignee: Hoya Corporation, Tokyo, Japan

[21] Appl. No.: 841,184

[22] Filed: Feb. 26, 1992

[30] Foreign Application Priority Data

Mar. 6, 1991 [JP] Japan ................................. 3-040250

[51] Int. Cl.$^5$ ........................................... C04B 35/48
[52] U.S. Cl. ..................................... 501/103; 501/104
[58] Field of Search .................. 501/103, 104; 106/35; 433/8

[56] References Cited

U.S. PATENT DOCUMENTS

| | | | |
|---|---|---|---|
| 4,915,625 | 4/1990 | Tsukuma et al. | 501/103 X |
| 5,059,562 | 10/1991 | Gentsu | 501/103 X |

FOREIGN PATENT DOCUMENTS

| | | |
|---|---|---|
| 64-46451 | 1/1989 | Japan . |
| 64-25847 | 2/1989 | Japan . |
| 0146451 | 5/1989 | Japan . |
| 3170148 | 7/1989 | Japan . |
| 2-21857 | 1/1990 | Japan . |
| 1311885 | 10/1991 | Japan . |

Primary Examiner—Karl Group
Attorney, Agent, or Firm—Nixon & Vanderhye

[57] ABSTRACT

An ivory-colored zirconia sintered body having high toughness, high mechanical strength and aesthetical excellence, a process for its production and its use as a bracket for orthodontic application; the sintered body containing stabilizer-containing $ZrO_2$ as a main component, and also containing, based on the stabilizer-containing $ZrO_2$, 0.05 to 1.0 mol % of $Er_2O_3$, 0.0001 to 0.05 mol % of $Pr_6O_{11}$, 0.0001 to 0.3 mol % of $Fe_2O_3$ and 0.05 to 0.3 mol % of ZnO; the process comprising either (A) calcining a powder obtained from a solution containing a zirconium compound, a compound which becomes a stabilizer after calcination and sintering, an erbium compound and a praseodymium compound, adding and mixing an iron compound and a zinc compound to/with the calcined powder, forming a shaped body from the resultant mixture and sintering the shaped body, or (B) adding and mixing an erbium compound, a praseodymium compound, an iron compound and a zinc compound to/with a stabilizer-containing zirconia powder while the first two compounds are in a solution state, forming a shaped body from the resultant mixture, and sintering the shaped body; and the zirconia sintered body being used as a bracket for orthodontic application.

6 Claims, No Drawings

IVORY-COLORED ZIRCONIA SINTERED BODY, PROCESS FOR ITS PRODUCTION AND ITS USE

BACKGROUND OF THE INVENTION

1. Field of the Invention

The present invention relates to an ivory-colored zirconia sintered body, a process for the production thereof and use thereof as a bracket for orthodontic application.

2. Prior Art

Due to high strength and excellent gloss of a mirror-polished surface, a zirconia sintered body, particularly a tetragonal zirconia sintered body, has been increasingly applied to the production of home utensils such as a knife, sports goods such as golf shoes and spikes or track shoes, while it has been also begining to be applied to the production of seals, accessories, frames and faces of watches and frames of ophthalmic lenses as a substitute for an ivory. Zirconias in a variety of colors are demanded in order to meet with these expanding requirements. In particular, a substitute for an ivory is desired to have a color closer to the natural color of an ivory. However, there is no report on a zirconia having such a color.

Meanwhile, stainless steel has been and is used as a material for a bracket for orthodontic application. That is because a bracket attached to each tooth is forcibly pulled with a wire made of a metal, etc., for orthodontic application and is therefore required to have high strength and high toughness so as to be free from snapping and chipping, and stainless steel meets with these requirements. However, stainless steel involves a defect in that it has metal gloss and shows its color, or is inferior when aesthetically appreciated. To overcome this defect, JP-A-64-25847 discloses a bracket for orthodontic application, which is formed from single crystal alumina. JP-A-64-46451 discloses a bracket for orthodontic application, which is formed from single crystal zirconia containing yttria. Further, JP-A-64-52448 discloses a bracket for orthodontic application, which is formed from spinel type crystalline ceramics obtained from magnesium oxide and aluminum oxide. Furthermore, JP-A-2-21857 discloses a bracket for orthodontic application, which is formed from a material prepared by incorporating iron oxide, manganese oxide, nickel oxide or a mixture of these into zirconia partially stabilized with yttria, etc.

The single crystal alumina described in the above JP-A-64-25847 is excellent in transparency and hence aesthetically satisfactory. However, this single crystal alumina has the following defects. Its processing requires a high cost. Since it has directional strength and low fracture toughness, it is liable to be snapped or chipped, and its broken surface forms a sharp edge like broken glass.

The single crystal zirconia containing yttria, described in the above JP-A-64-46451, and the spinel type crystalline ceramic described in the JP-A-64-52448 are transparent and aesthetically excellent. However, these materials have a defect in that they have low mechanical strength and are therefore liable to snap.

The partially stabilized zirconia containing a transition metal oxide such as iron oxide, etc., described in JP-A-2-21857 may exhibit a variety of colors. However, an ivory color cannot be obtained. And, when this partially stabilized zirconia is attached to teeth, it cannot be said to be aesthetically satisfactory, since it is poor in translucency.

SUMMARY OF THE INVENTION

It is therefore an object of the present invention to provide an ivory-colored zirconia sintered body having high toughness and high mechanical strength and being aesthetically excellent, a process for the production thereof, and use thereof as a bracket for othodontic application.

The present invention has been made to achieve the above object. The zirconia sintered body of the present invention contains, as a main component, stabilizer-containing $ZrO_2$, and also contains, based on the stabilizer-containing $ZrO_2$, 0.05 to 1.0 mol % of $Er_2O_3$, 0.0001 to 0.05 mol % of $Pr_6O_{11}$, 0.0001 to 0.3 mol % of $Fe_2O_3$ and 0.05 to 0.3 mol % of ZnO.

The process for the production of a zirconia sintered body having the above composition, provided by the present invention, comprises the following method (A) or (B).

Method (A)

This method comprises calcining a powder obtained from a solution containing a zirconium compound, a compound which becomes a stabilizer after the calcination and sintering, an erbium compound and a praseodymium compound, then adding and mixing an iron compound and a zinc compound to/with the calcined powder, shaping the resultant mixture into a shaped body and sintering the shaped body.

Method (B)

This method comprises adding and mixing an erbium compound, a praseodymium compound, an iron compound and a zinc compound to/with a zirconia power containing a stabilizer while the first two compounds are in a solution state, shaping the resultant mixture into a shaped body and sintering the shaped body.

Further, the bracket for orthodontic application is formed from a zirconia sintered body having the above composition.

DETAILED DESCRIPTION OF THE INVENTION

First, the zirconia sintered body of the present invention will be explained hereinafter.

The zirconia sintered body of the present invention contains a stabilizer-containing $ZrO_2$ as a main component. As a stabilizer, $Y_2O_3$ is the most preferred when the zirconia sintered body is required to have high strength (the amount of this stabilizer is 1.0 to 7.0 mol % based on the total amount of the stabilizer and $ZrO_2$). And, $CeO_2$ (10 to 16 mol %) ranks second in the preference. Further, CaO (8 to 12 mol %) and MgO (16 to 26 mol %) can be also used as a stabilizer when high strength is not necessarily required.

The zirconia sintered body of the present invention contains, based on the stabilizer-containing $ZrO_2$, 0.05 to 1.0 mol % of $Er_2O_3$, 0.0001 to 0.05 mol % of $Pr_6O_{11}$, 0.0001 to 0.3 mol % of $Fe_2O_3$ and 0.05 to 0.3 mol % of ZnO.

$Er_2O_3$, $Pr_6O_{11}$ and $Fe_2O_3$ work as a colorant, and impart a zirconia sintered body with a natural ivory color. The reason for the limitations of the amounts of the the $Er_2O_3$, $Pr_6O_{11}$ and $Fe_2O_3$ to the above ranges is as follows. When each of these amounts is less than the above corresponding lower limit, no effect of coloring is obtained. When each of these amounts exceeds the above corresponding upper limit, the resultant color can be no longer said to be an ivory color, and the sintered body properties are also adversely affected.

ZnO is a product to which the zinc compound used as a sintering aid has been converted by sintering. The reason for the limitation of the amount of ZnO to 0.05 to 0.3 mol % is as follows. When this amount is less than 0.05 mol %, the amount of the zinc compound as a sintering aid is too small, and an effect of the sintering aid is hardly exhibited. When this amount exceeds 0.3 mol %, the amount of the zinc compound is too large, and the sintered body properties are adversely affected.

The methods for the production of the above zirconia sintered body, provided by the present invention, will be described hereinafter. The present process for the production of the zirconia sintered body comprises Method (A) or Method (B) as described earlier.

Method (A)

At first, a powder containing a zirconium compound, a compound which becomes a stabilizer after the calcination and sintering, an erbium compound and a praseodymium compound is prepared from a solution containing these compounds. The method of forming the powder from the solution is selected from a coprecipitation method, an evaporation to dryness method, an oxalate method and a hydrolysis method.

The zirconium compound as a raw material is a compound which becomes zirconia after the calcination and sintering, and specific examples thereof include soluble zirconium compounds such as $ZrOCl_2$, $ZrO(NO_3)_2$, $ZrOSO_4$, $ZrO(C_2H_3O_2)_2$, $Zr(C_4H_9O)_4$ and $Zr(C_3H_7O)_4$. In the present invention, the term "soluble" means that a compound is dissolved or easily soluble in an aqueous medium such as water, and this term is used in this sense hereinafter. Examples of the compound which becomes a stabilizer ($Y_2O_3$, $CeO_2$, $CaO$, $MgO$, etc.) after the calcination and sintering include soluble compounds such as chlorides, nitrates and acetates of Y, Ce, Ca and Mr. The erbium compound and the praseodymium compound become $Er_2O_3$ and $Pr_6O_{11}$ after the calcination and sintering, and work as a colorant. Specific examples thereof include soluble erbium compounds and praseodymium compounds such as chlorides including $ErCl_3$ and $PrCl_3$ and nitrates including $Er(NO_3)_3$ and $Pr(NO_3)_3$.

The amount of the erbium compound and the praseodymium compound based on the above zirconium compound is set such that the amount of $Er_2O_3$ based on the stabilizer-containing $ZrO_2$ in the zirconia sintered body as a product is 0.05 to 1.0 mol % and that the amount of $Pr_6O_{11}$ on the same basis is 0.0001 to 0.05 mol %. The amount of the compound which becomes a stabilizer after the calcination and sintering is preferably set such that the stabilizer in a predetermined amount is present in the zirconia sintered body as a product; (Based on the total amount of the stabilizer and $ZrO_2$, the amount of $Y_2O_3$ is 1.0 to 7.0 mol %, the amount of $CeO_2$ is 10 to 16 mol %, the amount of $CaO$ is 8 to 12 mol %, and the amount of $MgO$ is 12 to 26 mol %).

In Method (A), the above-obtained powder is calcined. The calcining temperature is in the range of 800° to 1,100° C. The specific surface area of the calcined powder increases with a decrease in the calcining temperature, and decreases with an increase in the calcining temperature. Therefore, the calcining temperature may be selected depending upon the specific surface area of an intended powder. For example, for a powder having a specific surface area of 15 to 20 m²/g, the calcining temperature is set preferably around 900° C. For a powder having a specific surface area of 6 to 10 m²/g, the calcining temperature is set preferably in the range of 1,000° to 1,050° C.

In Method (A), an iron compound and a zinc compound are added to, and mixed with, the above calcined powder, and the resultant mixture is shaped and sintered to obtain the intended zirconia sintered body.

The iron compound becomes $Fe_2O_3$ after the calcination and sintering, and works as a colorant. Specific examples thereof include soluble iron compounds such as iron chloride, iron nitrate, iron acetate and iron acetylacetonate and insoluble iron compounds such as iron oxide, iron carbonate and iron hydroxide. In the present invention, the term "insoluble" means that a compound is not dissolved or hardly dissolved in an aqueous medium such as water, and this term is used in this sense hereinafter. The zinc compound works as a sintering aid, and is selected from any compounds which become ZnO after the calcination and sintering. Examples thereof include insoluble zinc compounds such as oxides and carbonates and soluble zinc compounds such as acetates and chlorides.

The amounts of the above iron compound and the above zinc compound are set at such amounts that the amount of $Fe_2O_3$ based on the stabilizer-containing $ZrO_2$ in the zirconia sintered body as a product is 0.0001 to 0.3mol % and that the amount of ZnO on the same basis is 0.05 to 0.3 mol %.

The shaping of the powder after the addition of the iron compound and zinc compound is carried out by any one of a cold isostatic press method, a die-molding method, an extrusion molding method and an injection molding method, whereby a shaped body is obtained depending upon the form of a zirconia sintered body as a product. Then, the shaped body is sintered under the following conditions. Although differing depending upon the specific surface area of the powder and the shaping pressure, in general, the sintering temperature is set in the range of 1,300° to 1,400° C. when the powder has a specific surface area of 6 m²/g and the shaping pressure is a hydrostatic pressure of 2 t/cm², and the sintering temperature is set in the range of 1,200° to 1,300° C. when the powder has a specific surface area of 15 m²/g and the shaping pressure is as described above, whereby a sintered body having at least 98% of the theoretical density is obtained. This sintering temperature is lower than the sintering temperature (1,450° to 1,500° C.) for any commercially available zirconia powder (specific surface area, 10 to 15 m²/g) by 200° to 300° C. The sintering time is in the range of 0.5 to 10 hours.

The thus-obtained zirconia sintered body exhibits bending strength equivalent to or higher than any commercially available zirconia sintered body (product having a $Y_2O_3$ content of 3 mol %). Further, the thus-obtained zirconia sintered body shows high fracture toughness. Moreover, the thus-obtained zirconia sintered body has an ivory color and is aesthetically excellent. It can be therefore used as a substitute for an ivory for seals, accessories, frames and faces of watches, frames of ophthalmic lenses, and the like. Further, it is used as a bracket for orthodontic application. This point will be detailed later.

Method (B)

In Method (B), an erbium compound, a praseodymium compound, an iron compound and a zinc compound are added to, and mixed with, a preliminarily prepared, stabilizer-containing zirconia powder while the first two compounds are in a solution state, and the resultant mixture is shaped and sintered, whereby a zirconia sintered body is obtained. The stabilizer-containing zirconia powder used in this Method (B) is prepared as follows. A solution containing any one of soluble zirconium compounds such as $ZrOCl_2$, $ZrO(NO_3)_2$, $ZrOSO_4$, $ZrO(C_2H_3O_2)_3$, $ZrO(C_4H_9O)_4$ and $ZrO(C_3H_7O)_4$ and any one of soluble compounds (chlorides, nitrates and acetates of Y, Ce, Ca and Mg) which become a stabilizer ($Y_2O_3$, $CeO_2$, $CaO$, $MgO$, etc.) after the calcination and sintering such as $YCl_3$, $Y(NO_3)_3$, $Y(C_2H_3O_2)_3$, $CeCl_3$, $Ce(NO_3)_3$, $Ce(C_2H_3O_2)_3$, $CaCl_2$, $Ca(NO_3)_2$, $MgCl_2$ and $Mg(NO_3)_2$ is subjected to a treatment by any one of a coprecipitation method, an evaporation to dryness method, an oxalate method and a hydrolysis method. Then, the resultant solid powder is dried and calcined.

The erbium compound and the praseodymium compound which are added to, and mixed with, the above-prepared stabilizer-containing zirconia powder become $Er_2O_3$ and $Pr_6O_{11}$ after the calcination and sintering, and work as a colorant. These compounds are required to be in a solution state when these are added to, and mixed with, the stabilizer-containing zirconia powder. These compounds are therefore selected from the same soluble compounds as those used in the above Method (A). Meanwhile, the iron compound and the zinc compound are not always required to be in a solution state when these are added to the stabilizer-containing zirconia powder. These compounds may be therefore selected from the same soluble compounds and the same insoluble compounds as those used in the above Method (A). The shaping and sintering are also carried out by the same methods as those used in Method (A), whereby the zirconia sintered body is obtained. Like the sintered body obtained by the above Method (A), the zirconia sintered body obtained by this Method (B) also exhibits bending strength equivalent to or higher than any commercially available zirconia sintered body (product having a $Y_2O_3$ content of 3 mol %) and exhibits high fracture toughness. The thus-obtained zirconia sintered body can be component-analyzed by chemical analysis and atomic absorption analysis. Having an ivory color, the thus-obtained zirconia sintered body can be used as a substitute for an ivory and further as a bracket for orthodontic application as will be described below.

The bracket for orthodontic application will be explained hereinafter. The bracket for orthodontic application, provided by the present invention, is formed of the above-described zirconia sintered body which contains, as a main component, stabilizer-containing $ZrO_2$, and also contains, based on the stabilizer-containing $ZrO_2$, 0.05 to 1.0 mol % of $Er_2O_3$, 0.0001 to 0.05 mol % of $Pr_6O_{11}$, 0.0001 to 0.3 mol % of $Fe_2O_3$ and 0.05 to 0.3 mol % of ZnO. As will be made clear in Examples which will follow, the present bracket for orthodontic application is aesthetically excellent and has high toughness and high mechanical strength. Therefore, it is excellent over any conventional bracket formed of a stainless steel and any conventional bracket formed of ceramic.

The zirconia sintered body constituting the bracket for orthodontic application of the present invention has a hardness, as a Vickers hardness, of 900 to 1,250 $kg/mm^2$, which is rather lower than the hardness of alumina. Since, however, for some patients, the bracket may contact an encountering tooth and wear it due to their dentin and dentition, the bracket is provided with a coating formed from a material having a hardness which is softer than, or close to, that of natural teeth (substantially, a Vickers hardness of 100 to 700 $kg/mm^2$), whereby the above wear can be prevented. The thickness of this coating is preferably 50 to 300 $\mu m$. When it is less than 50 $\mu m$, the coating is worn out, and when it exceeds 300 $\mu m$, the coating may disadvantageously peel off the bracket of the sintered body. The above coating is formed from a material selected from polymer resins such as an epoxy resin and polyurethane resin, a mixture of any one these with an inorganic material powdered filler such as alumina, magnesia or silica, and glass ceramic prepared by precipitation of mica crystallite. The zirconia sintered body is coated with the above coating directly or with an adhesive.

The present invention will be described more specifically by reference to Examples.

EXAMPLES 1-1 TO 1-5

An aqueous solution of $ZrOCl_2$, $YCl_3$, $ErCl_3$ and $PrCl_3$ was added dropwise to aqueous ammonia of which the pH was kept at 10, and the resultant coprecipitate was filtered. The remaining solid was washed with water, washed with an alcohol and dried at 110° C. The thus-obtained dry powder was calcined at 1,000° C. for 3 hours to give a powder having a specific surface area of about 6 $m^2/g$. An ethanol solution of zinc acetate and iron nitrate was added to the calcined powder, and these components were mixed by ballmilling for about one day. Then, the resultant slurry was solidified by evaporation to dryness to give a mixed powder. This mixed powder was shaped into bracket-formed bodies and test piece-form bodies for measurements of physical properties by an injection molding method, and degreased. Then, in an electric furnace, these shaped bodies were temperature-rised up to 1,300° C. at a rate of 100° C./hour, kept at 1,300° C. for 3 hours, cooled to 600° C. at a rate of 500° C./hour, and then cooled to room temperature still in the furnace.

By changing the amount of each component, the sintered bodies (brackets and test pieces) of Examples 1-1 to 1-5 were obtained. Table 1 shows the results of measurements of the test pieces for bending strength (JIS R 1601) and fracture toughness, $K_{IC}$, (an indentation microfracture method by Vickers indentation under a load of 30 kg). The sintered bodies of these Examples showed a high bending strength of 105 to 115 $kg/mm^2$ and a high $K_{IC}$ of 6.5 to 8.7 MPam$^{\frac{1}{2}}$.

Further, the bracket-formed sintered bodies were polished by barreling to give brackets having translucency and gloss and having a color tone similar to ivory-colored natural teeth as shown in Table 1.

COMPARATIVE EXAMPLES 1-1 to 1-4

Example 1 was repeated except that the amounts of some components were set outside the scope of the present invention to give sintered bodies. Table 1 shows the results of measurements of physical properties of these sintered bodies. As shown in Table 1, the bending strength was as low as 72 to 100 $kg/mm^2$, and the $K_{IC}$ was also as low as 5.0 to 6.0 MPam$^{\frac{1}{2}}$. The color tone each was also unsatisfactory.

TABLE 1

| Component | Composition (mol%) | | | | |
|---|---|---|---|---|---|
|  | Y$_2$O$_3$ | Er$_2$O$_3$ | Pr$_6$O$_{11}$ | Fe$_2$O$_3$ | ZnO |
| Ex. 1-1 | 1.5 | 1.0 | 0.001 | 0.001 | 0.3 |
| 1-2 | 2.0 | 0.5 | 0.002 | 0.005 | 0.2 |
| 1-3 | 2.6 | 0.1 | 0.002 | 0.01 | 0.5 |
| 1-4 | 2.0 | 0.5 | 0.01 | 0.005 | 0.1 |
| 1-5 | 1.5 | 1.0 | 0.002 | 0.1 | 0.2 |
| CEx. 1-1 | 1.5 | 2.0 | 0.001 | 0.001 | 0.3 |
| 1-2 | 2.0 | 0.5 | 0.1 | 0.001 | 0.2 |
| 1-3 | 2.6 | 1.0 | 0.001 | 0.5 | 0.3 |
| 1-4 | 2.0 | 0.5 | 0.001 | 0.001 | 0.8 |

| | Sintering temperature (°C) | Sintered body density (g/cm$^3$) | Bending strength (kg/mm$^2$) | K$_{IC}$ (MPam$^{\frac{1}{2}}$) | Color |
|---|---|---|---|---|---|
| Ex. 1-1 | 1,300 | 6.14 | 105 | 6.5 | ivory |
| 1-2 | 1,300 | 6.08 | 108 | 7.5 | ivory |
| 1-3 | 1,300 | 6.05 | 110 | 6.7 | ivory |
| 1-4 | 1,300 | 6.06 | 115 | 8.7 | ivory |
| 1-5 | 1,300 | 6.12 | 108 | 7.9 | ivory |
| CEx. 1-1 | 1,300 | 6.08 | 72 | 5.1 | pink |
| 1-2 | 1,300 | 6.05 | 100 | 6.0 | yellow |
| 1-3 | 1,300 | 6.10 | 76 | 5.0 | dark brown |
| 1-4 | 1,300 | 6.02 | 72 | 5.0 | ivory |

Ex = Example. CEx = Comparative Example

EXAMPLES 2-1 to 2-4

An aqueous solution of ZrOCl$_2$ and YCl$_3$ was added dropwise to aqueous ammonia of which the pH was kept at 10, and the resultant coprecipitate was filtered. The remaining solid was washed with water, washed with an alcohol and dried at 110° C. The thus-obtained dry powder was calcined at 1,000° C. for 3 hours to give a powder having a specific surface area of about 6 m$^2$/g. Then a methanol solution of erbium acetate and a methanol solution of praseodymium acetate as well as zinc carbonate and iron oxide were added to the above powder, and these components were mixed by ballmilling for about one day. The resultant slurry was solidified by evaporation to dryness to give a mixed powder. This mixed powder was cold-isostatic-pressed under a pressure of 2,000 kg/cm$^2$, and the shaped bodies were sintered in an electric furnace by temperature-rising up to 1,300° C. at a rate of 100° C./hour and keeping this temperature for 3 hours. Then, the sintered bodies were cooled to 600° C. at a rate of 500° C./hour, and then cooled to room temperature still in the furnace.

The thus-obtained sintered bodies were shaped by grinding into a bracket form and a test piece form for measurements of physical properties, and then the bracket and test pieces were hot-isostatic-pressed at 1,300° C. for 30 minutes.

By changing the amounts of some components, the sintered bodies of Examples 2-1 to 2-4 were obtained. As shown in Table 2, the sintered bodies obtained in these Examples showed a high bending strength of 98 to 105 kg/mm$^2$ and a high K$_{IC}$ of 6.1 to 7.2 MPam$^{\frac{1}{2}}$.

Further, the bracket-formed sintered bodies were polished by barreling to give brackets having translucency and gloss and having a color tone similar to ivory-colored natural teeth as shown in Table 2.

COMPARATIVE EXAMPLES 2-1 to 2-3

Example 2 was repeated except that the amounts of some components were set outside the scope of the present invention to give sintered bodies. Table 2 shows the results of measurements of physical properties of these sintered bodies. As shown in Table 2, the sintered bodies of Comparative Examples 2-1 and 2-3 had low bending strength values of 72 and 78 kg/mm$^2$, and also had low fracture toughness values of 4.8 and 5.1 MPam$^{\frac{1}{2}}$. All the sintered bodies of Comparative Examples 2-1 to 2-3 were unsatisfactory in color tone.

COMPARATIVE EXAMPLES 3-1 and 3-2

Example 2 was repeated except that the erbium acetate solution and the praseodymium acetate solution were replaced with a suspension of erbium oxide (Comparative Example 3-1) and a suspension of praseodymium oxide (Comparative Example 3-2) respectively to give sintered bodies. Table 2 shows the results of measurements of physical properties of these sintered bodies. As shown in Table 2, these sintered bodies were inferior in bending strength, fracture toughness, K$_{IC}$, and color tone.

TABLE 2

| Component | Composition (mol%) | | | | |
|---|---|---|---|---|---|
|  | Y$_2$O$_3$ | Er$_2$O$_3$ | Pr$_6$O$_{11}$ | Fe$_2$O$_3$ | ZnO |
| Ex. 2-1 | 1.5 | 1.0 | 0.0001 | 0.02 | 0.3 |
| 2-2 | 2.0 | 0.5 | 0.02 | 0.01 | 0.2 |
| 2-3 | 2.6 | 0.01 | 0.03 | 0.2 | 0.05 |
| 2-4 | 2.0 | 0.3 | 0.001 | 0.01 | 0.1 |
| CEx. 2-1 | 1.5 | 2.0 | 0.0001 | 0.02 | 0.3 |
| 2-2 | 2.0 | 0.5 | 0.08 | 0.01 | 0.3 |
| 2-3 | 2.6 | 0.5 | 0.001 | 0.5 | 0.3 |
| CEx. 3-1 | 1.5 | 1.0 | 0.0001 | 0.02 | 0.3 |
| 3-2 | 2.0 | 0.5 | 0.02 | 0.01 | 0.2 |

| | Sintering temperature (°C) | Sintered body density (g/cm$^3$) | Bending strength (kg/mm$^2$) | K$_{IC}$ (MPam$^{\frac{1}{2}}$) | Color |
|---|---|---|---|---|---|
| Ex. 2-1 | 1,300 | 6.12 | 102 | 6.2 | ivory |
| 2-2 | 1,300 | 6.10 | 100 | 7.2 | ivory |
| 2-3 | 1,300 | 6.02 | 98 | 6.1 | ivory |
| 2-4 | 1,300 | 6.04 | 105 | 6.3 | ivory |
| CEx. 2-1 | 1,300 | 5.98 | 72 | 4.8 | pink* |
| 2-2 | 1,300 | 6.02 | 103 | 6.2 | yellow* |
| 2-3 | 1,300 | 6.02 | 78 | 5.1 | brown |
| CEx. 3-1 | 1,300 | 5.70 | 58 | 4.0 | pink* |
| 3-2 | 1,300 | 5.92 | 69 | 4.7 | yellow* |

Ex = Example, CEx = Comparative Example
*irregular color

EXAMPLE 3

The brackets and test pieces obtained in Example 1 were dipped in a dispersion prepared by dispersing 10% by weight of the zirconia powder prepared in Example 1 in a commercially available, liquid polyurethane resin (RU-39, supplied by Nippon Polyurethane Co., Ltd), followed by curing to form a coating having a thickness of 120 μm and a Vickers hardness of 150 kg/mm$^2$ on the surface of each of the brackets and test pieces, whereby there were obtained brackets and test pieces each having a coating to prevent wearing of natural teeth and having gloss. The thus-coated brackets and test pieces showed no change in strength and toughness.

The zirconia sintered body of the present invention has high mechanical strength, high fracture toughness and a clear ivory color tone. Therefore, it can be expected to find a wide use as a seal, an accessory, an article for amusement and entertainment, an article of stationary, a watch part, a bracket for orthodontic application, and the like.

In particular, when the zirconia sintered body of the present invention is used as a bracket for orthodontic application, it is aesthetically excellent since it is close to natural teeth in color tone and gives a sense of translucency. Further, since a coating can be provided as required, the wear of an encountering tooth can be prevented.

What is claimed is:

1. An ivory-colored zirconia sintered body which contains, as a main component, stabilizer-containing $ZrO_2$, and which also contains, based on the stabilizer-containing $ZrO_2$, 0.05 to 1.0 mol % of $Er_2O_3$, 0.0001 to 0.05 mol % of $Pr_6O_{11}$, 0.0001 to 0.3 mol % of $Fe_2O_3$ and 0.05 to 0.3 mol % of ZnO.

2. A sintered body according to claim 1, wherein the stabilizer is selected from the group consisting of $Y_2O_3$, $CeO_2$, CaO and MgO.

3. A sintered body according to claim 2, wherein the stabilizer is $Y_2O_3$ and the $Y_2O_3$ is contained in an amount of 1.0 to 7.0 mol % based on a total amount of the stabilizer and $ZrO_2$.

4. A sintered body according to claim 2, wherein the stabilizer is $CeO_2$ and the $CeO_2$ is contained in an amount of 10 to 16 mol % based on a total amount of the stabilizer and $ZrO_2$.

5. A sintered body according to claim 2, wherein the stabilizer is CaO and the CaO is contained in an amount of 8 to 20 mol % based on a total amount of the stabilizer and $ZrO_2$.

6. A sintered body according to claim 2, wherein the stabilizer is MgO and the MgO is contained in an amount of 16 to 26 mol % based on a total amount of the stabilizer and $ZrO_2$.

* * * * *